US006659974B1

(12) United States Patent
Moss

(10) Patent No.: US 6,659,974 B1
(45) Date of Patent: Dec. 9, 2003

(54) SINGLE LUMEN GASTRO-INTESTINAL FEEDING-DECOMPRESSION TUBES

(76) Inventor: Gerald Moss, 4049 NY 150, W. Sand Lake, NY (US) 12196

( * ) Notice: Subject to any disclaimer, the term of this patent is extended or adjusted under 35 U.S.C. 154(b) by 113 days.

(21) Appl. No.: 09/692,564

(22) Filed: Oct. 19, 2000

(51) Int. Cl.$^7$ ................................................. A61M 1/00
(52) U.S. Cl. ........................................ 604/31; 604/537
(58) Field of Search ................................ 604/27, 30–31, 604/33–35, 48, 77, 79, 246–247, 250, 256–257, 264, 270, 275–276, 516, 537; 600/120, 156, 158–159; 137/455–456, 467, 458, 493, 496–497, 511, 527.6; 251/149.8–149.9, 153–156, 349, 354

(56) References Cited

U.S. PATENT DOCUMENTS

| | | | |
|---|---|---|---|
| 4,249,535 A | | 2/1981 | Hargest, III |
| 4,300,550 A | | 11/1981 | Gandi et al. |
| 4,543,089 A | * | 9/1985 | Moss ........................ 604/43 |
| 4,642,092 A | * | 2/1987 | Moss .................... 604/102.03 |
| 4,657,536 A | * | 4/1987 | Dorman ...................... 137/860 |
| 4,676,778 A | | 6/1987 | Nelson, Jr. |
| 4,705,501 A | * | 11/1987 | Wigness et al. ............ 604/175 |
| 5,071,405 A | | 12/1991 | Piontek et al. |
| 5,085,635 A | * | 2/1992 | Cragg .................... 604/102.03 |
| 5,098,378 A | | 3/1992 | Piontek et al. |
| 5,112,301 A | * | 5/1992 | Fenton et al. ............... 604/247 |
| 5,125,897 A | * | 6/1992 | Quinn et al. ................ 604/175 |
| 5,203,769 A | | 4/1993 | Clement et al. |
| 5,520,662 A | * | 5/1996 | Moss ........................ 604/246 |
| 5,573,504 A | | 11/1996 | Dorsey, III |
| 5,665,064 A | | 9/1997 | Bodicky et al. |
| 5,788,631 A | | 8/1998 | Fiddian-Green |
| 5,832,920 A | | 11/1998 | Field |
| 5,968,008 A | | 10/1999 | Grams |

* cited by examiner

*Primary Examiner*—LoAn H. Thanh
(74) *Attorney, Agent, or Firm*—Schmeiser, Olsen & Watts

(57) ABSTRACT

The present invention provides a single lumen gastro-intestinal tube for use in both delivering nutrition into the gastro-intestinal tract and aspirating excess materials from the gastro-intestinal tract. The single lumen tube may be delivered into the gastro-intestinal tract transnasally or surgically. The single lumen tube in accordance with the present invention includes a one-way valve which permits nutrition or other fluids to flow out of the tube and into the gastro-intestinal tract but which closes to prevent materials from being aspirated from the gastro-intestinal tract through the one-way valve. The single lumen tube also includes aspiration pores located proximately from the one-way valve. The aspiration pores perform the aspiration of air and excessive materials from the gastro-intestinal tract. Preferably, the aspiration pores are sized so as to filter any solids present in the gastro-intestinal tract from the aspirated material. A single lumen tube in accordance with the present invention may be used in alternating the delivery of nutritional or other materials to the gastro-intestinal tract and the aspiration of air and excessive material from the gastro-intestinal tract.

15 Claims, 2 Drawing Sheets

SINGLE LUMEN GASTRO-INTESTINAL FEEDING-DECOMPRESSION TUBES

BACKGROUND OF THE INVENTION

1. Field of the Invention

The present invention relates to feeding tubes used to deliver nutrition, fluids and medicine directly into the gastro-intestinal tract of patients unable to be fed normally. The present invention further relates to tubes used to aspirate fluid and air from a patient's gastro-intestinal tract. More specifically, this invention concerns a single lumen tube for use in both delivering nutrition, fluid, returned aspirate, and medication to the gastro-intestinal tract as well as aspirating air and excess fluid from the gastro-intestinal tract.

2. Description of the Prior Art

Frequently, hospital patients are unable to consume food normally. In these situations, it is often necessary to use a feeding tube to provide nutrition, fluids, and/or medicine. Such a tube is inserted into a patient's gastro-intestinal tract through the nose (nasogastric or nasoenteric tubes) or surgically by means of a gastrostomy or jejunostomy. Because adequate nutritional intake facilitates recovery, the proper use of a feeding tube can greatly benefit a patient. However, feeding tubes also pose some discomfort, and even some potential threats, to patients.

A number of commercially available feeding tubes exist. Unfortunately, all presently available feeding tubes suffer from a variety of deficiencies. One common problem is that a feeding tube may deliver the fluids (which include liquid nutrition, hydrating fluids, medicine and previously aspirated materials being returned to the patient) at a rate exceeding the ability of the gastro-intestinal tract to absorb said fluids. This results in an accumulation of fluid within the intestine. In particularly bad cases, accumulation of fluid causes distension of the intestine that leads to the temporary loss of all residual intestinal function. In rare cases, this intestinal distension may induce fatal vagal reflex circulatory changes. Severely ill, malnourished patients are most at risk for developing the complications of overfeeding and also most in need of the earliest optimum nutrition.

A patient's impaired digestive system may also produce too many digestive secretions for the patient to reabsorb immediately. A typical person secretes seven to eight liters of fluid per day, starting with saliva. All secretions normally are reabsorbed by the intestine, without net loss or gain of fluid for the body. Unfortunately, during recovery from surgery the level of secretions remains relatively constant, while the intestine's ability to absorb secretions typically is impaired, sometimes severely. The result can be a build up of fluid in the intestine, with the same detrimental side effects as found with over-feeding.

The problem of digestive secretions can be exacerbated by feeding. When concentrated nutrition is delivered to a patient's gastro-intestinal tract, the body's natural response is to produce digestive secretions to dilute the feedings and break down the complex nutrients for absorption by the intestine. However, if a patient's gastro-intestinal function is severely impaired only a portion of the total fluid may be absorbed. By way of example, for 2 ml of nutrition delivered to the gastro-intestinal tract, 10 ml of digestive secretions may be provided in response. The intestine temporarily may be capable of absorbing only 2 ml of fluid, resulting in a net increase of 10 ml to the volume of fluid in the gastro-intestinal tract. This scenario may be repeated as feedings continue, causing progressive intestinal distension which, in turn, further impairs intestinal function.

To avoid problems of overfeeding or excessive secretion build up during recovery, a patient's gastro-intestinal tract may be aspirated to remove excessive fluid. However, any secretions removed in this way must be measured and recorded. An equal volume of fluid must be returned to the body, usually intravenously, to avoid a net loss of fluids and dehydration of the patient.

The very presence of a nasal feeding tube stimulates swallowing by the patient, introducing additional air into the intestine. The presence of air within the gastro-intestinal tract interferes with the propulsion and absorption of nutrition and can be quite uncomfortable or painful to a patient. The use of an aspirating tube to remove air from the gastro-intestinal tract has been used to combat this problem.

Unfortunately, the use of a second tube for aspiration presents new problems. The introduction of a second tube only adds to the pain and discomfort experienced by a patient. Furthermore, if a separate second tube is used, it may be difficult to effectively locate it proximate to the feeding tube, thereby preventing it from aspirating excessive food present in the intestine. Attempts have been made to overcome the difficulties of feeding and aspirating with two separate tubes by combining them into a single construction with two lumens. Such structures are of necessity larger than a single lumen system. Placing two lumens in a single structure also decreases the flexibility of the structure, resulting in increased tissue trauma and discomfort to a patient. Fabricating a double lumen structure also presents increased production difficulties and costs.

The need exists, therefore, for a single lumen feeding tube capable of both delivering nutrition to the intestine as well as aspirating to remove excessive food, secretions, or air from the intestine. Such a tube should allow nutrition to be delivered to a patient's gastro-intestinal tract more distally, while further allowing the prompt removal of more proximal excessive fluids to avoid intestinal distension. Such a feeding tube should ideally be of a size and resilience to avoid undue discomfort to the patient, while still effectively performing nutritional delivery and aspiration. Furthermore, a tube is needed that allows for the duration and frequency of cyclical nutrition delivery to, and aspiration from, the gastro-intestinal tract to provide optimal absorption of nutrition while preventing an excessive accumulation of fluids.

SUMMARY OF INVENTION

The present invention comprises a single lumen feeding tube of delivering nutrition as well as performing aspiration of the intestine. The feeding tube includes a one way valve, which may comprise a flattened tip at its distal end, and a plurality of aspiration pores proximate to the feeding tip. While nutrition is being delivered through the feeding tube, the feeding tip remains open and delivers most of the nutrition more distally into the intestine. Whenever suction is applied to the feeding tube, the flattened feeding tip closes, allowing more proximal aspiration to occur only via the plurality of pores located proximate to the feeding tip.

BRIEF DESCRIPTION OF DRAWINGS

The invention may be better understood by reference to the drawings in which.

It should be appreciated that the drawings are for illustrative purposes and are not necessarily to scale.

DETAILED DESCRIPTION OF THE PREFERRED EMBODIMENT

The preferred embodiment of the present invention is illustrated in reference to the figures. A feeding tube in accordance with the present invention performs the delivery of nutrition and the aspiration of the intestine by alternating cycles of feeding and aspirating. During the feeding phase, liquid nutrition, fluids, medication and previously aspirated fluid (collectively referred to as "nutrition") are introduced via the feeding tube into the gastro-intestinal tract. During the aspiration phase, air and fluids are removed from the gastro-intestinal tract. Preferably, liquids aspirated from the gastro-intestinal tract will later be returned, so as to avoid dehydrating the patient. To accomplish this cycling, a pump apparatus capable of alternating between aspiration and the delivery of nutrition must be used in conjunction with the feeding tube. Alternatively, separate pumps may be used for aspiration and the delivery of nutrition. Depending upon the specific use of the feeding tube and the patient's condition and needs, a variety of cycle times and pumps may be desirable. However, one pump apparatus deemed particularly desirable for use with the present invention is described fully in a patent application filed herewith.

Figure 1:
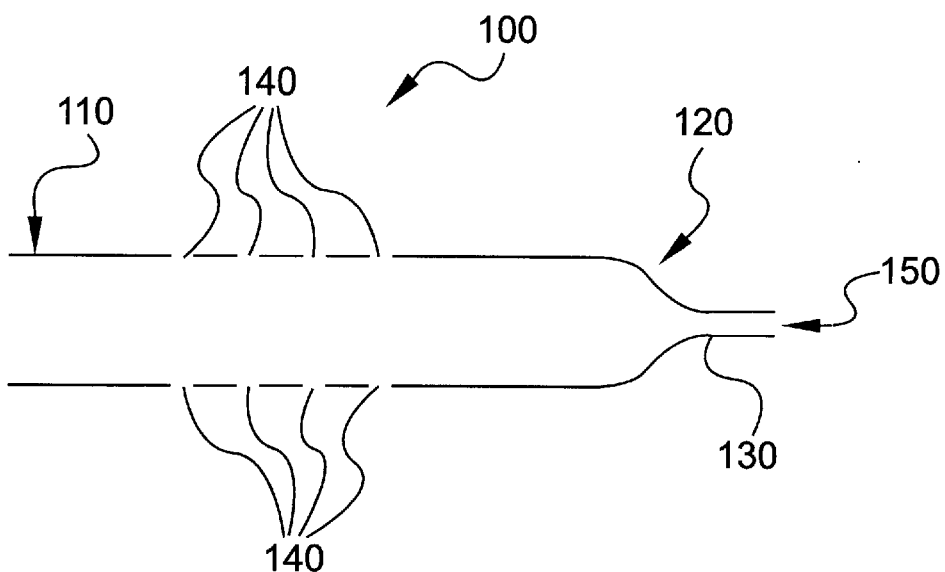
FIG. 1 is a cross-sectional view of a single lumen gastro-intestinal feeding-decompression tube in accordance with the present invention during the feeding cycle.
Figure 3:
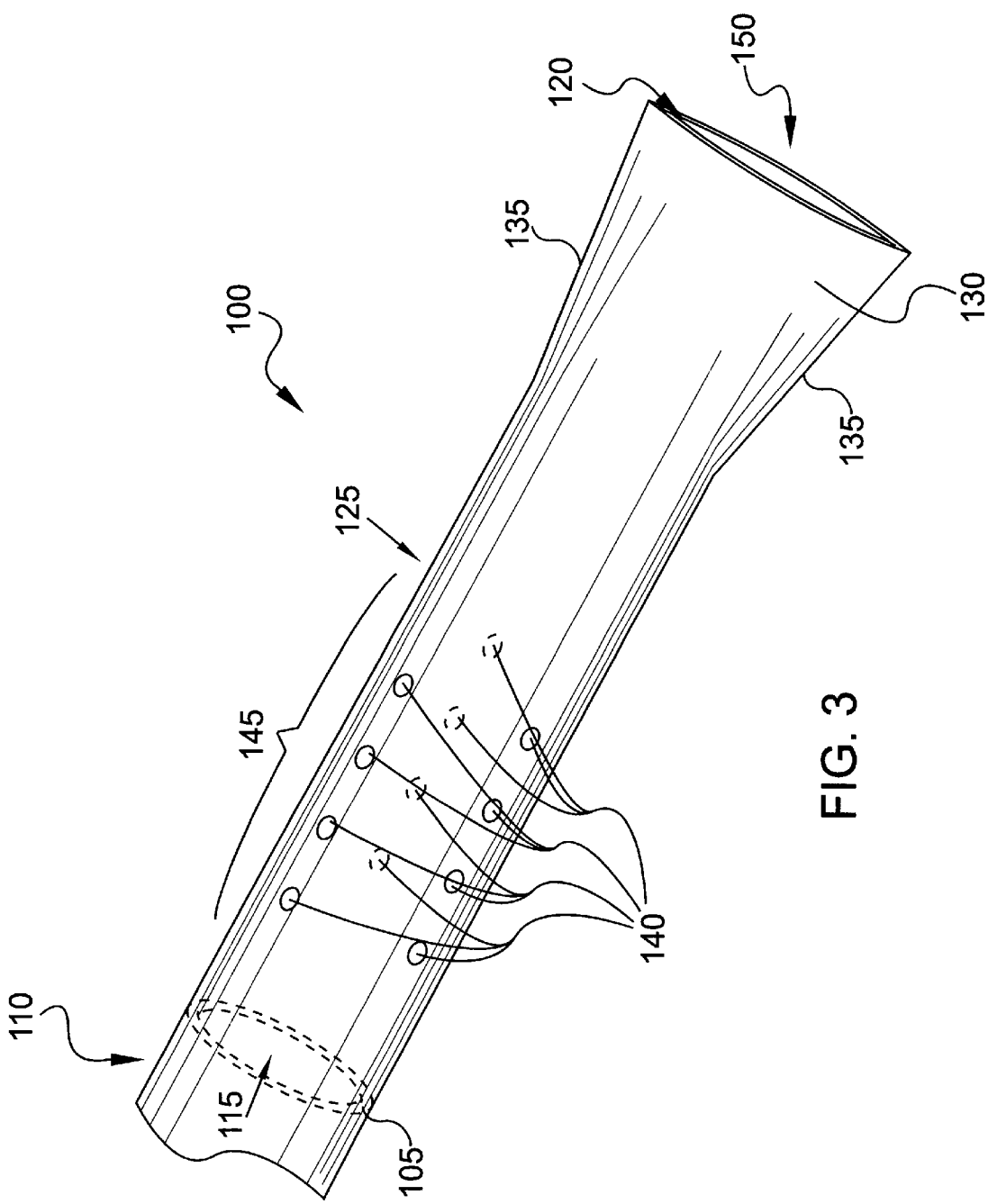
FIG. 3 is a perspective view of a single lumen gastro-intestinal feeding-decompression tube in accordance with the present invention during the feeding cycle.

FIG. 1 and FIG. 3 illustrate a feeding tube 100 in accordance with the present invention during the feeding cycle. The feeding tube 100 is typically constructed of polyurethane or other suitable material. Obviously, the material used to construct the feeding tube 100 should be medically acceptable and also must be pliable enough to allow insertion into a patient while being strong enough to withstand reasonable stresses. The feeding tube 100 preferably comprises a unitary elongate tube having a tube wall 105 defining a central lumen 115. The feeding tube 100 will typically have a substantially circular cross section, although no particular shape is required. The total length will be approximately 120 cm if the device is to be delivered transnasally, or approximately 50 cm if it is to be introduced surgically. The feeding tube 100 comprises a proximal end portion 110, a distal end portion 120 and a central portion 125, all of predetermined lengths. The proximal end portion 110 extends externally from the patient and is attached to the pump apparatus (not shown). The distal end portion 120 is used in the delivery of most of the nutrition into the more distal intestine. The central portion 125 is used in aspirating the more proximal intestine. The distal end portion 120 includes a feeding tip 130. In accordance with the preferred embodiment of the present invention, the feeding tip 130 is formed by flattening the terminal portion of the distal end 120 of the feeding tube 100. This forms creases 135 in the feeding tube 100, allowing the feeding tip 130 to collapse when suction is applied. As a result of the flattening, a feeding orifice 150 of the feeding tip 130 assumes an ovoid shape during delivery. The location of the feeding orifice 150 may vary. For example, the feeding orifice 150 may comprise the distal end 120 of the feeding tube 100, as shown in FIG. 3, or, in another embodiment, it may comprise an opening in the sidewall of feeding tube 100 proximate to the distal end 120. In accordance with the preferred embodiment of the present invention, the feeding tube 100 is constructed of a collapsible material so that the feeding tip 130 closes the feeding orifice 150 when suction is applied to the feeding tube 100. Preferably, the feeding tip 130 may be constructed so as to bias the feeding orifice 150 to a closed or collapsed position, such that the minimal pressure exerted by nutrition to be delivered into the intestine causes the feeding orifice 150 to open. Obviously, the feeding tip 130 may be constructed of a material different from the feeding tube 100, in which case the feeding tube 100 may be constructed of a more resilient material. In practice, however, the entire feeding tube 100, including the feeding tip 130, can be constructed of polyurethane. The feeding tube 100 may be constructed to allow a guide-wire (not shown) to be inserted through the central lumen 115 and out of the feeding orifice 150. The use of a guide-wire in this way facilitates the insertion and proper placement of the feeding tube 100.

The feeding tube 100 also includes an aspirating zone 145 in the central portion 125. In the aspirating zone 145, a plurality of openings (aspiration pores) 140 are formed through the tube wall 105 from the central lumen 115 to an area exterior to the tube 100. The plurality of aspiration pores 140 are located on the central portion 125 near the feeding tip 130 at the distal end 120 of the feeding tube 100, but more proximal than the feeding tip 130. The area of the aspiration pores 140 is small relative to the area of the feeding orifice 150. During a feeding cycle, most nutrition, typically over 90%, is delivered to the intestine via the feeding tip 130, and through the feeding orifice 150, with the remaining nutrition, approximately 10%, entering the intestine via the high resistance proximal aspiration pores 140. While it is desirable to deliver all of the nutrition via the more distal feeding tip 130 rather than the aspiration pores 140, the delivery of a small amount of nutrition via the aspiration pores 140 is not problematic. The bulk of the nutrition, which is initially distal to, and thereby shielded from, the aspiration pores, is given a greater opportunity to be absorbed by the intestine. If nutrition is not propelled and subsequently absorbed, it backs up in the intestine the short distance to the more proximal aspirating zone 135 where it will be removed safely.

By way of a more specific example of the preferred embodiment and best mode of the present invention, the material used for the feeding tube 100 may typically be thin walled polyurethane tubing having an outer diameter of approximately 2.7 to 4.7 mm and walls 105 approximately 0.4 mm thick. The size of the opening 150 of the feeding tip 130 will vary in accordance with the size of the tube 100. The feeding tip 130 may have a length of approximately 3.5 mm and a width of approximately 4.0 to 7.0 mm when flattened. During feeding, the feeding orifice 150 will approximate the size of the tubing itself, 2.7 to 4.7 mm. The plurality of aspiration pores 140 may comprise approximately 10 orifices having a diameter of between 0.25 mm and 0.45 mm. Thus the area of the feeding orifice 150 is approximately ten times the total area of the aspiration pores 140. The plurality of aspiration pores 140 may extend over approximately 15 cm of the distal end 120 of the feeding tube 100. The aspiration zone may appropriately begin approximately 7.5 cm from the terminus of the feeding tip 130 and extend to approximately 22.5 cm from the terminus of the feeding tip 130. Notwithstanding, the aspirating zone may comprise a 2 cm portion of feeding tube 100, and the aspirating zone may extend from about 1 cm to approximately 3 cm from a proximal end of feeding tip 130 of distal end 120.

Figure 2:
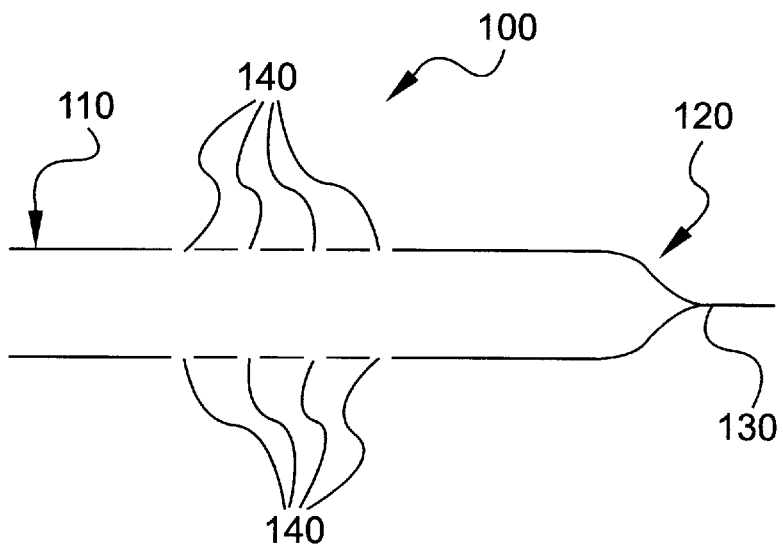
FIG. 2 is a cross-sectional view of a single lumen gastro-intestinal feeding-decompression tube in accordance with the present invention during the aspiration cycle.

Referring now to FIG. 2, a feeding tube in accordance with the present invention is shown during the aspiration cycle. During the aspiration cycle, suction is applied to the feeding tube 100 by the pump apparatus (not shown), causing it to draw material from the intestine. Because the feeding tube 100 is constructed of a flexible material such as thin polyurethane, the feeding tip 130 collapses along the creases 135 when the suction is applied, effectively cutting off flow through the feeding tip 130. In this way, the feeding tip 130 functions as a one-way flutter valve. This allows aspiration of air and excess liquid to proceed via the aspiration pores 140. It should be noted that the relatively small diameter of the aspiration pores 140 allows them to effectively filter any solids present in the intestine, thereby assuring that the aspirate can be returned via the feeding tube 100 without clogging the lumen or aspiration pores 140. The aspiration pores 140 will be placed at various locations around the feeding tube 100. If aspiration pores 140 on one side of the tube are blocked by contact with the intestinal wall, other aspiration pores 140 on the opposite side of the tube 100 will remain exposed and functional. The force exerted by the exposed aspiration pores 140 during aspiration will tend to reposition pores 140 in contact with the intestinal wall away from the intestinal wall.

As noted above, the feeding tip 130 functions as a one-way valve that allows nutrition to exit the feeding tube 100 but prevents aspirate from entering the feeding tube 100 through the feeding tip 130. One skilled in the art will realize that any one-way valve can be used for this purpose. For example, one-way valves using flaps or ball valves may be used in the feeding tip 130 without departing from the spirit of the invention. Using other types of one-way valves would allow the feeding tip 130 to assume other forms and shapes, which may be desirable in some instances. The preferred embodiment uses the feeding tip 130 itself as a one-way flutter valve to take advantage of simplified design, construction, and function. Not shown is a bullet shaped hollow shield surrounding the feeding tip 130. The internal diameter of the shield matches the external tubing's diameter, thus permitting unimpeded opening of the feeding tip 130 during feeding. Such a shield may be used to protect the feeding tip 130 during insertion of the feeding tube 100 and to facilitate the smooth insertion of the feeding tube 100.

It should be noted that after insertion into a patient's body the feeding tip 130 is positioned further down the intestine than the aspiration pores 140. Nutrition introduced to the gastro intestinal tract by the feeding tip 130 will proceed down the intestine and be absorbed. If the intestine is not functioning well, some nutrition introduced by the feeding tip 130, as well as excess secretions, will back up in the intestine to the more proximal aspiration pores 140. Thus, significant amounts of fluid will be removed from the intestine, but only in the event that there is a build up of fluid due to poor intestinal function. Air is always detrimental, as described previously, and is removed during aspiration.

While the feeding tube in accordance with the present invention may be used in conjunction with a variety of pumps and utilize a variety of feeding and aspirating cycles, the inventor contemplates the use of the following cycle. During the aspiration cycle, the pump will operate at a rate of approximately 5 ml per second to remove air and/or liquid from the intestine into a reservoir where the liquid will be held and the air vented. The aspiration will last for at least a predetermined amount of time, such as 5 seconds, and thereafter continue until the aspirate flow ceases. After aspiration concludes, nutrition will be delivered into the intestine. It is anticipated that nutrition will be delivered at a rate of 0.5 ml per second by reversing the pump immediately following the aspiration cycle. After the delivery of nutrition for a predetermined amount of time, such as for 4 seconds, resulting in a total of 2 ml of feeding solution being delivered, previously aspirated material may be returned to the gastro-intestinal tract via the feeding tube 100 to allow for reabsorption to maintain proper hydration. Aspiration may then resume, either immediately or after allowing a predetermined time to pass to allow absorption to occur.

After material has been aspirated, it should be held for return to the intestine during the next feeding cycle. This prevents the net loss of fluid from the intestine. It is contemplated that a 10 ml reservoir may be used for this purpose. Should more than 10 ml of aspirated fluid collect in the reservoir, the excess would go to an overflow tank. Excess fluid in the overflow tank would be measured and replaced in accordance with present hospital practice. It is anticipated that few patients would experience an overflow of the 10 ml reservoir during the use of the invention as described herein.

Obviously, numerous variations can be made to the present invention without departing from the scope and spirit of the invention and its broader aspects. For example, a variety of materials may be used to construct a feeding tube in accordance with the present invention. Likewise, the length and diameter of the feeding tube, the size of the feeding tip, and the size of the aspiration pores may be varied. Such variation may be particularly desirable to maximize effectiveness depending upon a patient's size and variations in tube placement. Likewise, the number of aspiration pores used may vary considerably without departing from the scope and spirit of the present invention. The particular type of pump and feeding mechanism used with a feeding tube in accordance with the present invention may vary depending upon the personal preference of doctors using the invention or the particularized needs of a patient. Likewise, a variety of nutritional products may be used in conjunction with the present invention. A precise cycle of feeding and aspirating used may be varied to suit the personal preferences of a physician and the needs of a patient.

What is claimed is:

1. A feeding and aspirating device comprising:
   a unitary elongate tube having a tube wall defining a central lumen, the tube having a distal end portion for placement within a patient's digestive system, a proximal end for placement exterior to the patient and a central portion of predetermined length, the central portion having an aspirating zone extending over a segment of the central portion proximate to the distal end portion, the aspirating zone having at least two openings between the central lumen and an area exterior to the tube, a first of the two openings at a first longitudinal distance from the distal end portion and a second of the two openings at a second longitudinal distance from the distal end portion, the second distance different than the first distance; and
   a feeding orifice in the distal end portion for communication between the central lumen and a feeding area exterior to the tube, the feeding orifice having a one way valve allowing a solution to pass through the tube and exit the feeding orifice and preventing substantially any flow into the central lumen through the feeding orifice.

2. The feeding and aspirating device of claim 1 wherein the tube wall surrounding the feeding orifice is collapsible, thus closing the orifice and serving as the one way valve.

3. The feeding and aspirating device of claim 2 wherein the feeding orifice in the opened position is between 2.7 and 4.7 mm in diameter.

4. The feeding and aspirating device of claim 3 wherein the size of the aspirating orifices are between 0.25 and 0.45 mm in diameter.

5. The feeding and aspirating device of claim 4 wherein the first aspirating orifice of the aspiration zone is about 7.5 cm from the feeding orifice.

6. The feeding and aspirating device of claim 5 wherein the aspiration pores are placed at various locations around the tube whereby the attachment of pores on one side of the tube to the organ wall during aspiration will tend to position the pores on the other side of the tube free from the organ wall.

7. The feeding and aspirating device of claim 5 wherein the relationship between the size and location of the aspirating orifices and the size and location of the feeding orifice is such that at least 90% of the solution pumped down toward the distal end and out of the tube will exit through the feeding orifice.

8. The feeding and aspirating device of claim 2 wherein the wall surrounding the feeding orifice is biased to the collapsed position.

9. The feeding and aspirating device of claim 2 wherein the wall surrounding the feeding orifice is biased to the opened position and aspirating through the tube causes the feeding orifice wall to collapse.

10. The feeding and aspirating device of claim 2 wherein the feeding orifice is at the absolute distal end whereby a guide-wire may extend through the central lumen and out of the feeding orifice for initial insertion of the tube into the patient.

11. A feeding and aspirating tube for use in a patient's intestine, the tube comprising:

a distal end located at the terminus of the feeding tube, the distal end comprising a one-way valve;

an aspirating zone located proximate to the distal end;

a plurality of pores within the aspirating zone, a first pore at a first longitudinal distance from the distal end and a second pore at a second longitudinal distance from the distal end, the second distance different than the first distance;

a central lumen communicating between the pores and the one-way valve at the distal end; and a proximal end for attachment to feeding and aspirating equipment.

12. The feeding tube of claim 11, wherein the aspirating zone comprises a 2 cm portion of the tube.

13. The feeding tube of claim 12, wherein the aspirating zone extends from about 1 cm to approximately 3 cm from a proximal end of a feeding tip portion of the distal end.

14. The feeding tube of claim 11, wherein the feeding tube comprises thin walled polyurethane tubing.

15. The feeding tube of claim 11, wherein the one-way valve comprises a flattened portion in which the distal end terminates.

* * * * *